(12) United States Patent
Ramage et al.

(10) Patent No.: US 9,822,055 B2
(45) Date of Patent: Nov. 21, 2017

(54) SILVER LOADED HALIDE REMOVAL RESINS FOR TREATING HALIDE CONTAINING SOLUTIONS

(71) Applicant: LyondellBasell Acetyls, LLC, Houston, TX (US)

(72) Inventors: David L. Ramage, Friendswood, TX (US); Noel C. Hallinan, Loveland, OH (US); Daniel F. White, Houston, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 0 days.

(21) Appl. No.: 15/189,467

(22) Filed: Jun. 22, 2016

(65) Prior Publication Data

US 2016/0376213 A1    Dec. 29, 2016

Related U.S. Application Data

(60) Provisional application No. 62/183,389, filed on Jun. 23, 2015.

(51) Int. Cl.
*C07C 51/12* (2006.01)
*C07C 51/47* (2006.01)
*B01J 41/04* (2017.01)
*B01J 47/06* (2006.01)
*B01J 41/14* (2006.01)

(52) U.S. Cl.
CPC .............. *C07C 51/12* (2013.01); *B01J 41/04* (2013.01); *B01J 41/14* (2013.01); *B01J 47/06* (2013.01); *C07C 51/47* (2013.01)

(58) Field of Classification Search
CPC ............ C07C 51/12; C07C 51/47; B01J 41/14
See application file for complete search history.

(56) References Cited

U.S. PATENT DOCUMENTS

| | | | | |
|---|---|---|---|---|
| 4,562,284 A * | 12/1985 | Drent | ................... | C07C 51/353 502/154 |
| 4,615,806 A * | 10/1986 | Hilton | ..................... | C07C 45/79 210/690 |
| 4,792,620 A * | 12/1988 | Paulik | .................. | B01J 31/0231 560/232 |
| 5,139,981 A * | 8/1992 | Kurland | ................... | B01J 39/05 210/683 |
| 5,344,976 A | 9/1994 | Jones et al. | | |
| 7,588,690 B1 | 9/2009 | Tsao | | |
| 2010/0113827 A1 | 5/2010 | Wang | | |
| 2016/0221910 A1* | 8/2016 | Shaver | ..................... | C07C 51/12 |

FOREIGN PATENT DOCUMENTS

EP         538040 A2    4/1993

OTHER PUBLICATIONS

PCT/US2016/038717 International Search Report and Written Opinion dated Aug. 10, 2016.

* cited by examiner

*Primary Examiner* — Paul A Zucker

(57) ABSTRACT

The present disclosure relates to methods of removing halides from a reactor effluent comprising treating the halide containing carbonylation product with a resin or material comprising a metal ion with a metal loading of greater than 15 wt % are provided herein. In some aspects, the methods involve treating the halide containing carbonylation product with a silver loaded resin which comprises a loading of greater than 15 wt % of silver to remove inorganic or organic halides.

11 Claims, No Drawings

SILVER LOADED HALIDE REMOVAL RESINS FOR TREATING HALIDE CONTAINING SOLUTIONS

CROSS-REFERENCE TO RELATED APPLICATIONS

This application claims benefit of priority to U.S. Provisional Application No. 62/183,389 filed on Jun. 23, 2015, which is incorporated herein by reference in its entirety.

BACKGROUND OF THE INVENTION

I. Field of the Invention

The present disclosure relates to silver loaded ion exchange resins for the removal of a halide from reactor effluent reaction product mixtures or product streams. In some aspects, the present disclosure provides a method of removing inorganic or organic iodides from an acetic acid process reactor or product stream.

II. Description of Related Art

Carbonylation processes often use transition metal catalysts and additives or promoters that contain halogens, typically iodide ions. For example, production methods for making glacial acetic acid may include lithium iodide and methyl iodide. Methyl iodide is often difficult to remove from carbonylation products. These halogen containing by-products or additives are passed along the process and can poison downstream process such as esterification or polymerization catalysts. For example, many of the catalysts used in the production of vinyl acetate are "poisoned" by iodide when it is present even at parts per billion (PPB) levels (please see U.S. Pat. No. 7,588,690; Jones, 2000; Haynes, 2010; and U.S. Pat. No. 5,139,981). As such, there is significant interest in methods and processes which reduce the amounts of these halogens, including processes where they may assist in carbonylation reaction(s).

One method of removing halides from a carbonylation reaction product is to pass the reactor effluent through an ion exchange resin with a cation. The cation, such as silver(I), binds the halide removing the halide from the effluent stream as described in U.S. Pat. No. 5,139,981. While U.S. Pat. No. 5,139,981 describes a wide array of silver loaded resins, traditionally, low levels of silver loading (i.e. loading of silver of less than 12%) are used because of cross reactivity of the resin with other carbonylation by-products or additives. Low levels of silver loading is typically utilized in order to maintain open sites for binding corrosion metals present in the reaction stream. Without sufficient open binding sites, the resin leaches silver ions from the resin to create the open binding sites to accommodate the corrosion metals. In particular, U.S. Pat. No. 5,139,981 notes that reaction products should be free from components such as corrosion metals, which can occupy empty binding sites or strip the loaded resin of silver(I). Higher iodide removal can be obtained at higher temperatures as described in U.S. Pat. No. 6,225,498, but higher temperatures detrimentally lead to thermal degradation of the resin and increased corrosion of the reactor. The increased corrosion further requires that the silver concentration be kept low in order to maintain open binding sites to bind the corrosion metals without displacing the bound silver.

Silver is an expensive starting material and the ion exchange resins used to remove iodide often preferentially bind protons or ions of corrosion metals such as iron, nickel, chromium and molybdenum over silver ions (please see U.S. Pat. No. 4,615,806). The removal of iron contaminants, a common by-product of the corrosion of the reactor, from glacial acetic acid was one of the first envisioned uses for the strong cation exchange resin Amberlyst™ 15 described in U.S. Pat. No. 4,615,806. If any of these types of ions are present, the silver on the silver loaded resin can be displaced for the higher binding metal and thus the ability of the resin to remove iodide is quickly eroded. The leaching of silver into the reaction mixture is a problem as noted in U.S. Pat. No. 5,801,279. Standard operational conditions likely lead to the leaching of the silver ions from the reactor bed; the inclusion of a downstream reactor bed to trap the entrained silver atoms is therefore recommended (U.S. Pat. No. 4,615,806). In an attempt to counter the reactivity of the resins to other corrosion metals, U.S. Pat. No. 5,220,058 replaces the sulfonic acid groups described in U.S. Pat. No. 5,139,981 with thiol groups, which are more resistant to metal exchange.

Methods have been undertaken to remove corrosive metals from reactor effluent to combat this problem. For instance, as described in U.S. Pat. No. 5,124,290 and WIPO Pat. App. Pub. No. WO 2005/107945, a first cation exchange resin may be used to remove the corrosion metals before the reaction effluent is further treated with a silver loaded resin. The introduction of an additional cation exchange resin bed increases the processing cost of purifying the reaction effluent. U.S. Pat. Nos. 6,642,168 and 6,657,078 highlight the importance of removing corrosion metals from the reaction mixture and utilizes two absorbent beds. In the first absorbent bed, the resin is not loaded with a metal that is reactive to halides so that corrosion metals can absorb selectively onto that bed and thus lower their concentration before entering the second metal containing bed. Additionally, in this method, the use of between 1 and 15 wt % is beneficial in the second metal containing bed as opposed to the 30-50 wt % disclosed in U.S. Pat. No. 5,139,981. Similarly, WIPO Pat. App. Pub. No. WO 2005/113479 treats the reaction effluent with a chelating agent, which removes the metal ions from the reaction. However, the chelating agents may bind the catalyst and promoter metals in lieu of binding the other corrosion metals and may not lower the concentration of the deleterious, corrosive metals. In addition, this method is not efficacious in preparing the reactor effluent for use of ion exchange resins to remove halides.

A need therefore exists for identifying methods which allow the use of high silver loaded resins to remove halides from a reactor effluent.

SUMMARY OF THE INVENTION

In one aspect, the present disclosure provides a method comprising:
  (A) reacting methanol, methyl acetate, or dimethyl ether with carbon monoxide to form acetic acid, wherein the reaction takes place in a reaction mixture further comprising a rhodium catalyst, an iodide source, and a phosphine oxide$_{(C \leq 24)}$ or substituted phosphine oxide$_{(C \leq 24)}$, wherein the iodide concentration is from 1,000 parts per million to 60,000 parts per million; and
  (B) purifying the reaction mixture using an ion exchange resin comprising from 15 to 40 wt % of silver(I) ions to produce a product mixture comprising greater than 60 wt % acetic acid and has an iodide concentration of less than 100 parts per million.

In some embodiments, the ion exchange resin is loaded with 18 wt % to 40 wt % of silver(I) ions, such as from 20 wt % to 40 wt % of silver(I) ions. In some embodiments, the iodide source is methyl iodide or hexyl iodide. In further embodiments, the iodide source is an inorganic iodide. In additional embodiments, the inorganic iodide is hydrogen iodide, hydroiodic acid, or lithium iodide. In some embodiments, the method further comprises distilling the product mixture to remove the rhodium catalyst and the phosphine oxide$_{(C \leq 24)}$ or substituted phosphine oxide$_{(C \leq 24)}$. In certain embodiments, the phosphine oxide$_{(C \leq 24)}$ or the substituted phosphine oxide$_{(C \leq 24)}$ is triphenylphosphine oxide.

In further embodiments, the reaction mixture comprises corrosive metals in a concentration of less than 5 parts per thousand (5 PPT). In some embodiments, the corrosive metals are ions of a transition metal or metals. In some embodiments, the transition metals are selected from Fe, Ni, Cr, Mo and combinations thereof. In some embodiments, the iodide concentration is less than about 1 part per million. In some embodiments, the iodide concentration is less than about 100 parts per billion.

In yet another aspect, the present disclosure provides a method comprising:
(A) either one of steps (1) and (2):
  (1) loading silver(I) ions onto an ion exchange resin until the silver(I) loaded ion exchange resin comprises 15 to 40 wt % of silver(I) ions; or
  (2) obtaining a silver(I) loaded ion exchange comprising 15 to 40 wt % of silver(I) ions; and
(B) obtaining a iodide containing acetic acid product stream wherein the product stream has an iodide concentration greater than 10 parts per billion; and
(C) contacting the product stream with the silver(I) loaded ion exchange resin under conditions sufficient to reduce the concentration of iodide in a final product stream.

In some embodiments, the iodide concentration of the product stream is from 50 parts per billion to about 100 parts per billion. In some embodiments, the concentration of iodide in the final product stream is reduced to less than 10 parts per billion. In some embodiments, steps (A) and (B) are performed in either order.

In still another aspect, the present disclosure provides a method comprising:
(A) either one of steps (1) and (2):
  (1) loading silver(I) ions onto an ion exchange resin until the silver(I) loaded ion exchange resin comprises 15 to 40 wt % of silver(I) ions; or
  (2) obtaining a silver(I) loaded ion exchange comprising 15 to 40 wt % of silver(I) ions; and
(B) obtaining a iodide containing an acetic acid reactor stream, wherein the reactor stream has an iodide concentration greater than 100 parts per million; and
(C) contacting the reactor stream with the silver(I) loaded ion exchange resin under conditions sufficient to reduce the concentration of iodide in a final reactor stream.

In some embodiments, the iodide concentration of the reactor stream is from 1,000 parts per million to about 60,000 parts per million. In some embodiments, the concentration of iodide in the final product stream is reduced to less than 1 part per million. In some embodiments, steps (A) and (B) are performed in either order.

In yet another aspect, the present disclosure provides a method comprising:
(A) obtaining a halide-containing carbonylation product mixture with a halide concentration greater than 50 parts per billion; and
(B) contacting the halide-containing carbonylation product mixture with the silver(I) loaded ion exchange resin wherein the silver(I) loaded ion exchange resin is loaded with from 15 wt % to 40 wt % silver(I) under conditions sufficient to reduce the halide concentration in the carbonylation product mixture to a final halide concentration less than about 10 parts per billion.

In some embodiments, the halide-containing carbonylation product is an iodide-containing carbonylation product mixture. In some embodiments, the carbonylation product is acetic acid.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the drawings and detailed description are to be regarded as illustrative in nature and not restrictive.

DETAILED DESCRIPTION OF THE INVENTION

In some aspects, the present disclosure provides a method of removing iodide from a reactor or product stream comprising treating the stream with a silver loaded resin. In some embodiments, the silver loaded resin has a high loading of silver ions which comprises greater than 15 wt % with silver ions. In certain embodiments, high loading of silver ion is greater than 20 wt % with silver ions. This method of removing iodide may be used to treat the effluent of a carbonylation process such as those used to make carboxylic acids. In some embodiments, the method is used to remove either inorganic or organic halides from the reactor effluent. In other embodiments, the method is used to remove either inorganic or organic halides from the product stream. In further embodiments, the effluent of a carbonylation process is the effluent of an acetic acid process. In some embodiments, the inorganic or organic halides are either inorganic or organic bromides or inorganic or organic iodides and combinations thereof.

I. METHODS OF REMOVING HALIDES FROM A REACTOR OR PRODUCT STREAM

In some aspects, the present disclosure relates to methods of using ion exchange resins to remove halides from carbonylation reaction products. A wide variety of ion exchange resins may be used in methods to remove halides from the carbonylation reaction process. One type of ion exchange resin which may be used in methods to remove halides includes macroreticular polymeric resins. Additionally, depending on the actual mechanism of removal and the amounts of halides, other resins such as mesoporous or gel may be used to remove the halides. As would be apparent to a skilled artisan, the selection of ion exchange resin depends on the reaction conditions and the identity and concentration of the halide. In some embodiments, the halide removed from the reactor stream or effluent is an iodide.

The use of macroreticular polymeric ion exchange resins include, but are not limited to, strongly acidic resins which are capable of binding cationic species. In some embodiments, the polymeric resins are discrete particles containing cross-linked polystyrene with divinyl benzene which contain active sites. The active sites of the resin are chemical groups in the resin which bind to agents which remove the halides from the solution. In some embodiments, these chemical groups are pH sensitive and protonation or deprotonation leads to the development of a charged species. In certain embodiments, the agents which remove the halides from the solutions are metals such as silver or mercury. In additional embodiments, the active sites of the resin are strongly acidic groups such as sulfonic acids or are weakly acidic groups such as carboxylic acids. In other embodiments, the active sites of the resin are chelating groups which binds to a metal ion. In some aspects, the resin binds to a metal ion, which complexes with a halide to remove the halide from the solution. In some embodiments, the ion exchange resin includes but is not limited to Amberlyst™ 15, Amberlite™ IR120, and Dowex™ Marathon C-10 Resin.

In some aspects, the ion exchange resins have a minimum number of active sites from about 1 equivalent to about 4 equivalents per liter. In further embodiments, the minimum number of active sites is from about 1.5 equivalents to about 3.0 equivalents per liter. In other embodiments, the amount of active sites in the ion exchange resin is at most less than about 8 equivalents per kilogram. In some embodiments, the amount of active sites is at most less than about 6 equivalents per kilogram. In additional embodiments, the amount of active sites is less than about 5 equivalents per kilogram. In other embodiments, any commercially available strongly acidic ion exchange resin is used to bind metal ions which remove halides from a solution.

In some aspects, the resin contains a percentage of cross-linking. In some embodiments, the amount of cross-linking is from about 1% to about 25%, such as from about 2% to about 15% and from about 4% to about 12%. In some embodiments, the particle size of the ion exchange resin has a harmonic mean size from about 0.1 mm to about 4 mm, including from about 0.2 mm to about 2 mm and from about 0.5 mm to about 1 mm. In other embodiments, the uniformity coefficient of the ion exchange resin particles is from about 1.1 to about 4, such as from about 1.5 to about 2. In further aspects, the particle size is highly uniform and contains less than 10% of particles outside the range from 0.3 mm to 1.2 mm, including less than 5% of particles are outside the range from 0.3 mm to about 1.2 mm. In certain aspects, it is contemplated that the size of the particles changes when exposed to solvent or water. In some embodiments, the particles exhibit swelling from the dry state to the aqueous state of greater than 25%, including greater than 35%.

In other aspects, the surface area of the ion exchange resin promotes the interaction of the solution containing the halide with the active site of the resin. In some embodiments, the ion exchange resin has a surface area greater than about 30 m$^2$/g, such as greater than about 50 m$^2$/g. In other aspects, the ion exchange resin has an average pore diameter of greater than 15 nm, including greater than about 25 nm. Additionally, in some aspects, the pore volume of the ion exchange resin is greater than 0.2 mL/g, such as greater than about 0.3 mL/g. It is contemplated that other reaction conditions and characteristics of the ion exchange resin affect the ability of the resin to bind metals such as silver which can assist in the removal of halides from a solution. These reaction conditions and characteristics may be optimized by a skilled artisan without undue experimentation.

As would be apparent to a person of skill in the art, the method of metal loading on the resin is inconsequential to the final product or its ability to remove halides from a reaction mixture. In some embodiments, the resin is chelated to a halide reactive metal. In some non-limiting embodiments, the metals which can be chelated to the ion exchange resin include palladium, mercury, or silver. In some embodiments, the metal loading of the resin comprises greater than about 12 wt %, including greater than 15 wt %. In some embodiments, the metal loading is greater than about 20 wt %, such as greater than about 22 wt % and greater than 12, 13, 14, 15, 16, 17, 18, 19, 20, 21, 22, 23, 24, 25, 26, 28, 30, 32, 34, 35, 36, 38, or 40 wt %, or any range derivable therein. In some embodiments, the metal loading is from about 12 wt % to about 24 wt %, such as from about 15 wt % to about 24 wt %.

In other aspects of the present disclosure, materials such as zeolites, silica, or alumina can be used a resin beds for removing halides from a reaction mixture. In some embodiments, the reactive metal is deposited on any solid support which is stable to the reaction stream. In the case of an acidic reaction stream, alumina or carbonate based supports are susceptible to degradation of the resin. In other aspects, it is envisioned that the solid support is a carbonaceous support such as graphite, activated charcoal, bone char, lignite, or other carbon based materials. For instance, U.S. Pat. No. 4,615,806 provides non-limiting examples of carbonaceous materials which may be used to remove halides.

In some aspects, the resin bed can be exposed to the reaction effluent at a temperature from about 0° C. to about 150° C., such as from about 0° C. to about 50° C. In other embodiments, the reaction effluent is exposed to the resin bed at an elevated temperature from about 50° C. to about 150° C., including from about 50° C. to about 100° C., from about 0° C. to about 100° C. and from about room temperature to about 25° C. In some aspects, the resin bed with a loading of greater than 15 wt % of silver has a bed lifetime of greater than about 275 hours, such as greater than about 300 hours and greater than about 400 hours.

II. REACTION OR PRODUCT STREAM OR EFFLUENT

The use of ion exchange resins may be used to remove halides from a reaction effluent, the product stream, or other reaction mixture. In some embodiments, the reactor effluent is from a carbonylation reaction, such as from the production of a carboxylic acid. In certain embodiments, the carboxylic acid is glacial acetic acid. In some aspects, the present disclosure relates to methods of removing halides from a reaction effluent of a carbonylation process in which the reaction effluent contains a low amount of corrosion metals. In further embodiments, the present disclosure describes removing iodide from a product stream which has been partially purified. In additional embodiments, the product stream has been largely purified except for a final halide removal step.

In some aspects, the present disclosure comprises a reactor effluent comprising a concentration of a halide ion of greater than about 1 part per million such as greater than about 2 parts per million and greater than about 5 parts per million. In some aspects, the method results in a reduction of the halide concentration of greater than about 50%, including greater than about 75%. In certain embodiments, the reduction comprises reducing the concentration of the halide to less than about 100 parts per billion, including less than about 10 parts per billion. In further aspects, the reactor effluent is purified such that the resultant solution comprises greater than about 90% acetic acid, including greater than about 95% acetic acid and greater than about 98% acetic acid.

In one aspect, the present disclosure relates to a method of removing halides from a reaction effluent from a carbonylation process which contains phosphine oxide and a transition metal catalyst. In some embodiments, the transition metal catalyst is a rhodium catalyst. It is contemplated that any rhodium carbonylation catalyst may be used in the carbonylation process described herein. In some aspects, the rhodium catalyst comprises a rhodium source selected from rhodium metal, rhodium halides, rhodium oxide, rhodium acetate, organorhodium compounds, coordination compounds of rhodium, or similar rhodium compounds. Additionally, mixtures of different rhodium sources may also be used. Non-limiting examples of rhodium sources which can be used in the carbonylation process include $RhCl_3$, $RhBr_3$, $RhI_3$, $RhCl_3.3H_2O$, $RhBr_3.3H_2O$, $RhI_3.3H_2O$, $Rh_2(CO)_4Cl_2$, $Rh_2(CO)_4Br_2$, $Rh_2(CO)_4I_2$, $Rh_2(CO)_8$, $Rh(CH_3CO_2)_2$, $Rh(CH_3CO_2)_3$, $Rh[(C_6H_5)_3P]_2(CO)I$, $Rh[(C_6H_5)_3P]_2(CO)Cl$, elemental Rh, $Rh(NO_3)_3$, $Rh(SnCl_3)[(C_6H_5)P]_2$, $RhCl(CO)[(C_6H_5)As]_2$, $RhI(CO)[(C_6H_5)Sb]_2$, $Rh[(C_6H_5)_3P]_2(CO)Br$, $Rh[(n-C_4H_9)_3P]_2(CO)Br$, $Rh[(n-C_4H_9)_3P]_2(CO)I$, $RhBr[(C_6H_5)_3P]_3$, $RhI[(C_6H_5)_3P]_3$, $RhCl[(C_6H_5)_3P]_3$, $RhCl[(C_6H_5)_3P]_3H_2$, $[(C_6H_5)_3P]_3Rh(CO)H$, $Rh_2O_3$, $[Rh(C_3H_4)_2Cl]_2$, $K_4Rh_2Cl_2(SnCl_2)_4$, $K_4Rh_2Br_2(SnBr_2)_4$, $[H][Rh(CO)_2I_2]$, $K_4Rh_2I_2(SnI_2)_4$, or is a complex of the formula $[Rh(CO)_2X_2][Y]$, wherein X is a halide and Y is a proton, an alkali metal cation, or a quaternary compound of nitrogen, phosphorus, or arsenic, or is a similar rhodium complex. In some embodiments, the rhodium source is $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, or $[H][Rh(CO)_2I_2]$. In further embodiments, the rhodium source is $Rh(CH_3CO_2)_2$, $Rh(CH_3CO_2)_3$, or $[H][Rh(CO)_2I_2]$.

The rhodium compound or complex may be used in a concentration sufficient to achieve a reasonable amount of carbonylation or an effective rate of carbonylation. Without being bound by theory, excess amounts of the rhodium catalyst can lead to the undesired by-products. Thus, the optimization of the rhodium catalyst is one factor which can directly impact the rate, amount, and yield of the carbonylation product. In a carbonylation process, the concentration of the rhodium catalyst that may be used is from 10 ppm to about 4000 ppm, including from about 200 ppm to about 1200 ppm and about 400 ppm to about 1000 ppm. These concentrations can also be expressed using molarity. In some embodiments, the concentration is from about $1\times10^{-4}$ M to about $4\times10^{-2}$ M, from about $2\times10^{-3}$ M to about $1.2\times10^{-2}$ M and from about $4\times10^{-3}$ M to about $1\times10^{-2}$ M. While these concentrations are sufficient to cause carbonylation to proceed, higher concentrations may be used so long as they do not cause an unsatisfactory extent of by-products.

In some aspects, the present disclosure relates to reactor streams or reactor effluents of a carbonylation process that is conducted in liquid phase or in gas phase. In further embodiments, the carbonylation reaction contains one or more liquid components that may be selected from acetic acid, methanol, water, methyl iodide, or methyl acetate and combinations thereof.

In some aspects, the carbonylation reaction comprises adding methyl acetate as a reaction component at a concentration from about 0.5 wt % to about 10 wt % of the total weight of the liquid reaction component. In some embodiments, the methyl acetate weight percentage correlates to a molarity of the methyl acetate from about 0.07 M to about 1.4 M. In certain embodiments, the amount of methyl acetate added to the liquid reaction component is from about 1 wt % to about 8 wt %. In further embodiments, the methyl acetate can be charged into the reactor. In other embodiments, the methyl acetate is formed in situ. In some embodiments, the amount of methyl acetate is added to produce a ratio between methyl acetate and the rhodium catalyst from about 1000:1 to about 2:1, such as a the ratio from about 700:1 to about 5:1 and from about 275:1 to about 14:1.

In some aspects, the reactor effluent is produced from a carbonylation process which comprises a liquid medium and comprises an iodide source. In certain embodiments, the iodide source is methyl iodide or hydroiodic acid. In some embodiments, the methyl iodide is added directly to the reaction mixture. In other embodiments, the methyl iodide can be generated in situ from the reaction of hydroiodic acid with methanol. Without being bound by theory, it is believed that the methyl iodide disproportionates and adds to the rhodium catalyst as a methyl cation and an iodide anion to form the active catalyst complex. A variety of different concentrations of the iodide source may be used in the carbonylation reaction of the present disclosure. In some embodiments, the amount of methyl iodide added to the reaction comprises a concentration from about 0.6 wt % to about 36 wt % of the liquid reaction component, such as from about 3.6 wt % to about 24 wt % of the liquid reaction component. The amount of methyl iodide can also be determined as a molarity of the liquid reaction component. In some embodiments, the concentration of methyl iodide is from about 0.05 M to about 3.0 M, including from about 0.3 M to about 2.0 M. In other embodiments, hydroiodic acid (HI) is used as the iodide source. In other embodiments, HI is used as the iodide source. In some embodiments, the concentration of hydroiodic acid or hydrogen iodide used in the carbonylation reaction is from about 0.6 wt % to about 23 wt %, including from about 2.3 wt % to about 11.6 wt %. The concentration of the hydroiodic acid or hydrogen iodide can be measured as the molarity of the liquid reaction component. In some embodiments, the concentration of hydroiodic acid or hydrogen iodide is from about 0.05 M to about 2.0 M, such as from about 0.2 M to about 1.0 M.

In some aspects, the carbonylation reaction further comprises adding a carboxylic acid to the liquid reaction component. In some embodiments, the carboxylic acid is acetic acid. In some embodiments, the concentration of acetic acid added to the liquid reaction component is from 20 wt % to about 80 wt % or when measured in molarity from about 3.0 M to about 12.0 M, such as about 35 wt % to about 65 wt % or when measured in molarity is from about 5 M to about 10 M. In some embodiments, the balance of the liquid reaction component is acetic acid.

In some aspects, the carbonylation reaction further comprises adding a second metal compound to the reaction mixture. In some embodiments, the second metal is a transition metal or a post-transition metal. In other embodiments, the carbonylation reaction further comprises adding one or more compounds or complexes of a metal selected from ruthenium, rhenium, osmium, cadmium, zinc, mercury, gallium, indium, or tungsten and combinations thereof. In some embodiments, any soluble or heterogeneous source of ruthenium can be added to the reaction mixture to enhance the yield and production of the carbonylation process. Some non-limiting examples of ruthenium compounds or complexes that can be used in the carbonylation reaction include ruthenium halides, ruthenium carbonyl, ruthenium oxides, ruthenium carboxylates, ruthenium carbonyl complexes, organoruthenium complexes such as tetrachlorobis(benzene)diruthenium(II), dichloro(cycloocta-1,5-diene) ruthenium(II) polymer, or tetrachlorobis(4-cumene)diruthenium(II) or mixed ruthenium halocarbonyls compounds such as dichlorotricarbonylruthenium(III) dimers or dibromotricarbonyl-ruthenium(II) dimers. In some embodiments, the concentration of the second metal added to the liquid reaction component is added relative to the carbonylation catalyst. In further embodiments, the amount of the second metal relative to the carbonylation catalyst is from about 0.1:1 to about 20:1, including from about 0.5:1 to 10:1 and from about 2:1 to about 10:1. In additional embodiments, the second metal is added to the reaction medium at a concentration up to the limit of solubility of the second metal in the reaction mixture. In some embodiments, the concentration of the second metal is less than about 8000 ppm, including about 400 ppm to about 7000 ppm.

In one aspect, the carbonylation process further comprises water in the reaction mixture. In some embodiments, the water is added deliberately to the reaction mixture. In other embodiments, the water is a contaminant from the addition of other components. Without being bound by theory, it is believed that the addition of water promotes the final conversion of the carbonylated compound into the appropriate carboxylic acid from the acid halide. The amount of water added to the reaction at a concentration from about 4 wt % to about 12 wt % relative to the total weight of the reaction mixture or in terms of molarity the amount of water is from about 2.5 M to about 7.5 M, including from about 4 wt % to about 11 wt % or about 2.5 M to about 7.0 M and from about 4.4 wt % to about 9 wt % or about 2.7 M to about 6.0 M. The amount of water can, in some embodiments, be measured relative to the amount of catalyst used in the reaction. In some embodiments, the ratio of water to catalyst is from about 200:1 to about 4000:1, such as from about 270:1 to about 1750:1.

In some aspects, the carbonylation process further comprises the addition of one or more gaseous compounds to the reaction mixture. In one embodiment, one of the gases added to the reaction mixture is hydrogen gas. Without being bound by theory, it is believed that the addition of hydrogen to the reaction mixture, particularly a reaction mixture comprising a rhodium catalyst, decreases the selectivity of the carbonylation process favoring the production of by-products such as aldehydes and alcohols. Furthermore, without being bound by theory, the carbonylation reactions which comprise hydrogen also exhibit increased catalytic efficacy. The amount of hydrogen used gas depends on the catalyst and other reactive metal components employed, as well as the identification of the desired products. In some embodiments, the ratio of hydrogen relative to the CO in the reaction mixture is from about 2:1 to about 1:8, such as from about 1:1 to about 1:4. In some embodiments, the concentration of the hydrogen added to the reaction mixture is from about 0.1 mol % to about 5 mol % based upon the amount of CO added to the reactor. In certain embodiments, the concentration of hydrogen is from about 0.5 mol % to about 3 mol %. In further embodiments, the hydrogen gas is added to the reactor as a separate stream from the other gaseous components. In other embodiments, the hydrogen gas is added as a mixture with CO. In some embodiments, hydrogen gas can be added to the reaction mixture as needed in order to maintain a consistent concentration of hydrogen gas in the reaction mixture. As CO is consumed in the reaction, in some embodiments, the molar ratio of hydrogen to CO can increase to a concentration from about 1000:1 to about 100:1. As the molar ratio of hydrogen to CO changes, in some embodiments, more CO is added to the reaction mixture to increase the molar ratio of hydrogen to CO.

In some aspects, the carbonylation reaction comprises adding CO to the reaction mixture. In some embodiments, the CO can be added as a gas. In other embodiments, the CO is generated in situ from the ligands of one or more of the metal catalysts. In certain embodiments, CO is added at a pressure from about 70 kPa to about 5,600 kPa. In additional embodiments, CO is added at a pressure from about 325 kPa to about 3,500 kPa. In some embodiments, CO is added at a pressure from about 650 kPa to about 2,100 kPa. In further embodiments, the reaction comprises continuous addition of CO to the reaction mixture to maintain a constant molar ratio of CO as the CO is consumed in the reaction.

In some aspects, the present disclosure provides a carbonylation process which can be carried out using a wide variety of different reactor systems. In some embodiments, the carbonylation process is carried out in a batch mode reactor. In other embodiments, the carbonylation process is carried out in a continuous mode reactor. In further embodiments, the carbonylation process is carried out in a fixed bed or fluidization reactor.

In some embodiments, the carbonylation method of the present disclosure is conducted under an increased pressure. In some embodiments, the reaction pressure is from about 1350 kPa to about 8,500 kPa, such as from about 2,000 kPa to about 4,200 kPa and about 2,800 kPa. Additionally, in further embodiments the temperature of the carbonylation reaction is elevated above room temperature. In some embodiments, the temperature of the carbonylation reaction is greater than 100° C., such as from about 150° C. to about 225° C., from about 160° C. to about 220° C., from about 170° C. to about 200° C. and about 175° C.

The reaction effluent of the carbonylation process includes the use of a phosphine oxide in production of a carboxylic acid in an amount relative to the rhodium catalyst. It is contemplated that any amount of phosphine oxide may be used in the reaction process. In some embodiments, the amount of phosphine oxide used is sufficient to stabilize the rhodium carbonylation catalyst, such as greater than 50 equivalents per equivalent of rhodium catalyst and greater than 100 equivalents per equivalent of rhodium catalyst. The amount of phosphine oxide used can also be described in terms of a concentration of the reaction mixture. In some embodiments, the amount of phosphine oxide used is from about 0.2 M to about 3.0 M, such as from about 0.4 M to about 1.4 M. In some embodiments, the concentration of the phosphine oxide is sufficient to achieve an improvement in some process metric such as increased rate, increased yield, or decreased production of one or more by-products. Without being bound by theory, the addition of phosphine oxide prevents the precipitation of the active rhodium catalyst and thus maintains the rate of the carbonylation reaction.

In another aspect, the carbonylation method further comprises adding an iodide salt. It is contemplated that the iodide anion is the important element in the salt for the reaction and as such, the identity of the cation is not important and thus an iodide salt with any cation may be used in the carbonylation reaction described herein. In some embodiments, the iodide salt is a metal iodide salt. In some embodiments, the metal is a Group 1, Group 2, or transition metal cation. In some embodiments, the metal is a Group 1 or Group 2 metal cation. In some embodiments, the metal is an alkali metal cation. In some embodiments, the metal is lithium and the metal iodide salt is lithium iodide. In some embodiments, the iodide salt is an organic cation iodide. In some embodiments, the organic cation is a quaternary organic cation. In some embodiments, the quaternary organic cation comprises a positively charged quaternary nitrogen atom. The concentration of lithium iodide which may be used in the carbonylation method varies widely and is dependent on the concentration of the reactive component. Without being bound by theory, the ratio of lithium iodide to methyl acetate, methanol, dimethyl ether, or other reactive intermediates used within the carbonylation reaction affects the reaction rate. In some embodiments, the concentration of the iodide salt is from about 1 wt % to about 30 wt % or from about 0.075 M to about 2.25 M, from about 2 wt % to about 20 wt % or from about 0.075 M to about 1.5 M and from about 10 wt % to about 20 wt % or from about 0.75 M to about 1.5 M. In some embodiment, the lithium to rhodium catalyst is in a molar ratio is greater than 38:1 and greater than 75:1. In some embodiments, the lithium to rhodium catalyst is in a molar ratio sufficient to stabilize the rhodium catalyst.

In other embodiments, the reaction conditions comprise using a low concentration of a metal iodide, such as less than 5 wt % and less than 4 wt %. In some embodiments, when the co-catalyst or promoter is added to the reaction, the concentration of the metal iodide is less than 3.5 wt %, including less than 3.0 wt %, less than 2.5 wt %, less than 2.0 wt % and less than 1.5 wt %. In further embodiments, the concentration of metal iodide correlates to the total concentration of iodide in the reactor. In additional embodiments, the concentration of iodide in the reactor comprises iodide from the metal catalyst, metal co-catalysts or promoters, or the addition of a metal iodide like lithium iodide (LiI). In some embodiments, the concentration of iodide is measured by titration of $AgNO_3$ into a sample of the reaction media and measuring the amount of silver iodide that precipitates from the solution.

Any carbonylation process which results in an effluent with low concentrations of corrosive metals may be used with metal loaded resins of the present disclosure. In some embodiments, the concentration of corrosive metals is less than 50 parts per thousand, less than 10 parts per thousand, less than 1 part per thousand and less than 750 parts per million. In some embodiments, the corrosive metals are transition metal ions. In some embodiments, the transition metal ions include, but are not-limited to, ions of molybdenum, iron, nickel, or chromium and combinations thereof. In some embodiments, the transition metal ions include other metals present in the carbonylation process such as rhodium, rhenium, ruthenium, osmium, cadmium, zinc, mercury, gallium, indium, or tungsten.

In other embodiments, a product stream from a carbonylation reactor is used. The product stream may be used partially purified. In some embodiments, the product stream has been subjected to purification by distillation, extraction, flashing, phase separation, or other purification techniques. In other embodiments, the product stream has been purified except for a final halide removal step. In some embodiments, the product stream comprises less than about 250 parts per million of the corrosion metals, such as less than about 100 parts per million.

III. PROCESS SCALE-UP

The above referenced methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012), which is incorporated by reference herein.

IV. DEFINITIONS

When used in the context of a chemical group, "halide" means a halogen atom formulated as an anion bearing a single negative charge or a compound which contains a halogen atom. In some embodiments, a halogen atom is a fluoride, chloride, bromide, or iodide.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "alkyl," when used without the "substituted" modifier, refers to a monovalent saturated aliphatic group with a carbon atom as the point of attachment, a linear or branched, cyclo-, cyclic or acyclic structure, and no atoms other than carbon and hydrogen. Thus, as used herein cycloalkyl is a subset of alkyl, with the carbon atom that forms the point of attachment also being a member of one or more non-aromatic ring structures, wherein the cycloalkyl group consists of no atoms other than carbon and hydrogen. As used herein, the term does not preclude the presence of one or more alkyl groups (carbon number limitation permitting) attached to the ring or ring system. The term "alkanediyl," when used without the "substituted" modifier, refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. It is noted that while the alkenediyl group is aliphatic, once connected at both ends, this group is not precluded from forming an aromatic structure. When any of these terms is used with the "substituted" modifier one or more hydrogen atoms has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The term "haloalkyl" is a subset of substituted alkyls, in which one or more hydrogen atoms has been substituted with a halo group and no other atoms aside from carbon, hydrogen and halogen are present. The group, —CH$_2$Cl, is a non-limiting example of a haloalkyl. The term "fluoroalkyl" is a subset of substituted alkyl, in which one or more hydrogen has been substituted with a fluoro-group and no other atoms aside from carbon, hydrogen and fluorine are present.

Similar to the term "alkyl" as defined above, other chemical groups are defined according to IUPAC nomenclature in combination with the descriptions shown below. The term "alkenyl" refers to a monovalent unsaturated aliphatic group with a carbon atom as the point of attachment, a linear or branched acyclic structure, at least one nonaromatic carbon-carbon double bond, no carbon-carbon triple bonds, and no atoms other than carbon and hydrogen. The term "aryl" refers to a monovalent unsaturated aromatic group with an aromatic carbon atom as the point of attachment, where the carbon atom forms part of one or more six-membered aromatic ring structures, the ring atoms are carbon, and the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. The term "aralkyl" refers to the monovalent group-alkanediyl-aryl, in which the terms alkanediyl and aryl are each used in a manner consistent with the definitions herein and with IUPAC nomenclature. The term "heteroaryl" refers to a monovalent aromatic group with an aromatic carbon atom or nitrogen atom as the point of attachment, where the carbon atom or nitrogen atom forming part of one or more aromatic ring structures, at least one of the ring atoms is nitrogen, oxygen or sulfur, and the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. When any of these terms is used with the "substituted" modifier, one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$OC(O)CH_3$, or —$S(O)_2NH_2$. The suffix "diyl" on a chemical group refers to the divalent group form of that chemical group.

The term "alkoxy," when used without the "substituted" modifier, refers to the group —OR, in which R is an alkyl, as that term is defined above. The terms "cycloalkoxy," "alkenyloxy," "aryloxy," "aralkoxy" and "heteroaryloxy", when used without the "substituted" modifier, refers to groups, defined as —OR, in which R is cycloalkyl, alkenyl, aryl, aralkyl and heteroaryl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. The term "ester" corresponds to a group of the general formula RC(O)R', wherein R is an alkyl group and R' is an alkoxy group. The term "carboxylic acid" corresponds to a group of the general formula RC(O)OH, wherein R is an alkyl group. When any of these terms is used with the "substituted" modifier, one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$OC(O)CH_3$, or —$S(O)_2NH_2$.

The term "phosphine oxide," when used without the "substituted" modifier, refers to a compound of the formula O=$PR_3$ or a diphosphine oxide as that term is defined below, wherein each R is independently hydrogen, alkyl, cycloalkyl, alkenyl, aryl, aralkyl, or heteroaryl as those terms are defined above. Non-limiting examples include $OPMe_3$ (trimethylphosphine oxide) and $PPh_3O$ (triphenylphosphine oxide). The term "diphosphine oxide," when used without the "substituted" modifier, refers to a compound of the formula $R_2$—P(O)-L-P—$R_2$ or $R_2$—P(O)-L-P(O)—$R_2$, wherein each R is independently hydrogen, alkyl, cycloalkyl, alkenyl, aryl, aralkyl, or heteroaryl, and wherein L is a divalent group including alkanediyl, cycloalkanediyl, alkenediyl, arenediyl, aralkanediyl, or heteroarenediyl. The term "phosphine oxide" also includes oxides of the phosphines described in U.S. Pat. App. Pub. No. 2006/0173212. When any of these terms is used with the "substituted" modifier, one or more hydrogen atoms attached to a carbon atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$OC(O)CH_3$, or —$S(O)_2NH_2$.

The use of the word "a" or "an," when used in conjunction with the term "comprising" in the claims and/or the specification, may mean "one," but it is also consistent with the meaning of "one or more," "at least one," and "one or more than one."

Throughout this application, the term "about" is used to indicate that a value includes the variation of error for the device, the method being employed to determine the value, or the variation that exists among the study subjects. The term "about" when used in the context of epoxidation process conditions is used to imply the natural variation of conditions and represent a variation of plus or minus 5% of the measurement. In some embodiments, the variation is plus or minus 1% of the measurement.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The terms "corrosive metals" and "corrosion metals," as used in the context of this application, include transition metals in the effluent stream which bind to the ion exchange resin. In some aspects, the predominant corrosion metals are nickel, iron, molybdenum, and chromium but the presence of other metals is also contemplated. In some embodiments, a reaction mixture which contains a low level of corrosion metals is a reaction mixture that contains less than 2 parts per thousand of nickel, iron, molybdenum, and chromium and combinations thereof. In other embodiments, the amount of nickel, iron, molybdenum, and/or chromium is less than 1 part per thousand.

As used herein, an "iodide source" is an inorganic compound wherein at least one of the anions is iodide or an alkyl iodide such as methyl iodide or hexyl iodide. In some embodiments, the inorganic compound is an inorganic iodide such as a metal iodide or a hydrogen iodide. Some non-limiting examples of metal iodides include sodium iodide, potassium iodide, or lithium iodide. In some embodiments, inorganic iodides also include hydrogen iodide/hydroiodic acid.

A "method" is series of one or more steps that lead to a final product, result or outcome. As used herein, the word "method" is used interchangeably with the word "process."

The term "product stream" used in the context of this application refers to the product output of a carbonylation reaction which has been further purified to remove the reaction catalysts, co-catalysts, or by-products. In some embodiments, the reactor stream has been passed through one or more purification or separation steps. In some embodiments, the product stream has been purified except for a final halide removal step.

The terms "reactor stream" or "reactor effluent" are used interchangeably in this application to refer to the output of a reactor. In some embodiments, the terms refer to the output passing through a separation or purification process after being subjected to the carbonylation process.

The above definitions supersede any conflicting definition(s) in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present technology.

V. EXAMPLES

The following examples are included to demonstrate certain embodiments of the disclosure. It should be appreciated by those of skill in the art that the techniques disclosed in the examples which follow represent techniques discovered to function well in the practice of the technology. However, those of skill in the art should, in light of the present disclosure, appreciate that many changes can be made in the specific embodiments which are disclosed and still obtain a like or similar result without departing from the spirit and scope of the technology.

Example 1

Preparation of Silver Loaded Resin

A. Preparation of 14.2 wt % Ag on Amberlyst™ 15

Silver oxide (5.387 g) was placed in a two liter (L) flask, and then glacial acetic acid (600 mL) and water (600 mL) were added. While stirring, the slurry was slowly heated to 50° C., and was maintained at that temperature until complete dissolution had taken place and the solution was colorless. With continued stirring, Amberlyst™ 15 (dry) (30.002 g) was added slowly and then stirred for an additional 3 h. The impregnated resin was filtered while hot and then washed with 3 portions of 50° C. water. The resin was then allowed to air dry overnight at ambient temperature. XRF analysis indicated that the actual loading was 14.2 wt % Ag.

Example 2

Iodide Removal Tests

A. Hexyl Iodide Concentration Determination

Hexyl iodide concentrations in acetic acid were determined by gas chromatography (GC) utilizing an electron capture detector (ECD). Calibration standards of 61.4, 12.3 and 6.1 ppm were prepared by dilution of gravimetrically prepared stock solutions.

B. Experimental Description

The iodide removal unit consisted of a jacketed column with a 0.43" inner diameter. Iodide removal resin was held in the column with glass wool and silicon carbide. Hot oil was pumped through the jacket of the jacketed column to maintain an internal temperature of 125° F. A solution of hexyl iodide (50 ppm) in acetic acid was pumped through the column at a rate of 12 bed volumes per hour. The effluent from the bed, after passing through uninsulated tubing and cooling to ambient temperature, was periodically sampled and analyzed for hexyl iodide concentration.

C. Amberlyst® 15 Based Resin with Silver Concentration Used Commercially to Remove Organic Iodides from Glacial Acetic Acid The resin prepared in Example 1 was utilized to remove hexyl iodide as described above. The resin bed operated for 260 hours before the hexyl iodide concentration in the effluent exceeded 10 ppb.

D. Amberlyst™ 15 Based Resin with High Silver Concentration

A commercial resin consisting of Amberlyst™ 15 (dry) with a concentration of 23.5 wt % Ag was utilized to remove hexyl iodide as described in Example 2, Section B. The bed operated for 425 hours before the hexyl iodide concentration began to exceed 10 ppb.

All of the compounds, complexes, and methods disclosed and claimed herein can be made and executed without undue experimentation in light of the present disclosure. While the compounds, complexes, and methods of this technology have been described in terms of certain embodiments, it will be apparent to those of skill in the art that variations may be applied to the compounds, complexes, and methods, as well as in the steps or in the sequence of steps of the method described herein without departing from the concept, spirit, and scope of the disclosure. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the technology as defined by the appended claims.

What is claimed is:

1. A method for producing acetic acid comprising:
(A) reacting methanol, methyl acetate, or dimethyl ether with carbon monoxide to form acetic acid at a pressure of about 1350-8500 kPa, wherein the reaction takes place in a reaction mixture further comprising a rhodium catalyst, an iodide source, and a phosphine oxide$_{(C \leq 24)}$ or substituted phosphine oxide$_{(C \leq 24)}$, wherein the iodide concentration is from 1,000 parts per million to 60,000 parts per million; and
(B) purifying the reaction mixture using an ion exchange resin comprising:
(i) either one of steps (1) and (2):
(1) loading silver(I) ions onto an ion exchange resin until the silver(I) loaded ion exchange resin comprises 15 to 40 wt % of silver(I) ions; or
(2) obtaining a silver(I) loaded ion exchange comprising 15 to 40 wt % of silver(I) ions; and
(ii) obtaining a iodide containing acetic acid product stream comprising an iodide concentration of 50-100 parts per billion; and
(iii) contacting the product stream with the silver(I) loaded ion exchange resin to reduce the concentration of iodide in a final product stream.

2. The method of claim 1, wherein the ion exchange resin is loaded with 18 wt % to 40 wt % of silver(I) ions.

3. The method of claim 2, wherein the ion exchange resin is loaded with 20 wt % to 40 wt % of silver(I) ions.

4. The method of claim 1, wherein the iodide source is methyl iodide or hexyl iodide.

5. The method of claim 1, wherein the iodide source is an inorganic iodide.

6. The method of claim 5, wherein the inorganic iodide is hydrogen iodide, hydroiodic acid, or lithium iodide.

7. The method of claim 1, further comprising distilling the product mixture to remove the rhodium catalyst and the phosphine oxide$_{(C \leq 24)}$ or substituted phosphine oxide$_{(C \leq 24)}$.

8. The method of claim 1, wherein the reaction mixture comprises transition metals selected from the group consisting of Fe, Ni, Cr, Mo and combinations thereof at a concentration of less than 5 parts per thousand.

9. The method of claim 1, wherein the phosphine oxide$_{(C \leq 24)}$ or the substituted phosphine oxide$_{(C \leq 24)}$ is triphenylphosphine oxide.

10. The method of claim 1, wherein the concentration of iodide in the final product stream is reduced to less than 10 parts per billion.

11. A method for reducing the iodide concentration in acetic acid comprising:
(A) obtaining an acetic acid mixture produced in accordance with claim 1 with an iodide concentration of greater than 50 parts per billion; and
(B) contacting the iodide containing acetic acid mixture with the silver(I) loaded ion exchange resin, wherein the silver(I) loaded ion exchange resin is loaded with from 15 wt % to 40 wt % silver(I) under conditions sufficient to reduce the iodide concentration in the acetic acid mixture to a final iodide concentration less than 10 parts per billion.

\* \* \* \* \*